(12) United States Patent
Carmeliet et al.

(10) Patent No.: US 7,357,929 B2
(45) Date of Patent: Apr. 15, 2008

(54) PLACENTAL GROWTH FACTOR AS A TARGET FOR THE TREATMENT OF OSTEOPOROSIS

(75) Inventors: Peter Carmeliet, Blanden (BE); Désiré Collen, Winksele (BE); Roger Bouillon, Winksele (BE); Gertrudis Carmeliet, Blanden (BE)

(73) Assignees: D. Collen Research Foundation VZW, Leuven (BE); K.U. Leuven Research & Development, Leuven (BE); Vlaams Interuniversitair Instituut Voor Biotechnologie VZW, Zwijnaarde (BE)

( * ) Notice: Subject to any disclaimer, the term of this patent is extended or adjusted under 35 U.S.C. 154(b) by 0 days.

(21) Appl. No.: 10/519,330

(22) PCT Filed: Jun. 27, 2003

(86) PCT No.: PCT/EP03/50274

§ 371 (c)(1),
(2), (4) Date: Apr. 25, 2005

(87) PCT Pub. No.: WO2004/002524

PCT Pub. Date: Jan. 8, 2004

(65) Prior Publication Data

US 2005/0175609 A1    Aug. 11, 2005

(30) Foreign Application Priority Data

Jun. 28, 2002    (EP)    ................... 02077591

(51) Int. Cl.
*A61K 39/00*    (2006.01)
*C07K 14/475*    (2006.01)
(52) U.S. Cl. .................... 424/134.1; 530/350
(58) Field of Classification Search .......... None
See application file for complete search history.

(56) References Cited

U.S. PATENT DOCUMENTS 5,670,057 A    9/1997    Chen et al.

6,369,204 B1    4/2002    Kim et al.
2002/0009750 A1    1/2002    Rockwell et al.

FOREIGN PATENT DOCUMENTS

JP    2001086982 A    *    4/2001
WO    PCT/EP01/05478        11/2001
WO    PCT/US02/19505        1/2003

OTHER PUBLICATIONS

Robinson et al. Nonvascular role for VEGF: VEGF4-1, 2 activity is critical for neural retinal development. FASEB, vol. 15, pp. 1215-1217 (May 2001).*
Dias et al. Inhibition of both paracrine and autocrine VEGF/VEGF-2 signaling pathways is essential to induce long-term remission of xenotransplanted human leukemias. PNAS, vol. 98, No. 19, pp. 10857-10862 (Sep. 2001).*
Carmeliet et al., "Synergism Between Vascular Endothelial Growth Factor and Placental Growth Factor Contributes to Angiogenesis and Plasma Extravasation in Pathological Conditions", *Nature Medicine*, 7:575-583 (2001).
Mayr-Wohlfart et a l., "Vascular Endothelial Growth Factor Stimulates Chemotactic Migration of Primary Human Osteoblasts", *Bone*, 30:472-477 (2002).
Niida et al., "Vascular Endothelial Growth Factor Can Substitute for Macrophage Colony-stimulating Factor in the Support of Osteoclastic Bone Resorption", *Journal of Experimental Medicine*, vol. 190:293-298 (1999).
Laurin et al. "Paget Disease of Bone: Mapping of Two Loci at 5q35-qter and 5q31." Am. J. Hum. Genet. 69: 528-542 (2001).

* cited by examiner

*Primary Examiner*—Marianne P. Allen
*Assistant Examiner*—Regina M Deberry
(74) *Attorney, Agent, or Firm*—Clark & Elbing LLP

(57) ABSTRACT

This invention relates to antagonists of placental growth factor and signalling thereof, pharmaceutical compositions containing such antagonists and the use of such antagonists to prevent bone loss or bone mass and to enhance bone healing including the treatment of conditions which present with low bone mass and/or bone defects in vertebrates, and particularly mammals, including humans.

1 Claim, No Drawings

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: a peptide to which there is antigen specificity

<400> SEQUENCE: 1

Gly Ser Lys Leu Lys Asp Pro Glu Leu Ser Leu Lys Gly Thr Gln His
 1               5                  10                  15

Ile Met Gln Ala
            20
```

PLACENTAL GROWTH FACTOR AS A TARGET FOR THE TREATMENT OF OSTEOPOROSIS

CROSS REFERENCE TO RELATED APPLICATIONS

This application is the U.S. National Stage of International Application No. PCT/EP2003/050274, filed Jun. 27, 2003, which was published in English under PCT Article 21(2), and which claims the benefit of European patent application 02077591.2, filed Jun. 28, 2002.

FIELD OF THE INVENTION

This invention relates to antagonists of placental growth factor and signalling thereof, pharmaceutical compositions containing such antagonists and the use of such antagonists to prevent bone loss or bone mass and to enhance bone healing including the treatment of conditions which present with low bone mass and/or bone defects in vertebrates, and particularly mammals, including humans.

BACKGROUND OF THE INVENTION

Osteoporosis is a systemic skeletal disease, characterised by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly with the ageing of the population. World-wide fracture incidence is forecasted to increase three-fold over the next 60 years, and one study estimated that there will be 4.5 million hip fractures world-wide in 2050. Women are at greater risk of osteoporosis than men. Women experience a sharp acceleration of bone loss during the five years following menopause. Other factors that increase the risk include smoking, alcohol abuse, a sedentary lifestyle and low calcium intake. There are currently two main types of pharmaceutical therapy for the treatment of osteoporosis. The first is the use of anti-resorptive compounds to reduce the resorption of bone tissue. Estrogen is an example of an anti-resorptive agent. It is known that estrogen reduces fractures. In addition, Black, et al. in EP 0605193A1 report that estrogen, particularly when taken orally, lowers plasma levels of LDL and raises those of the beneficial high density lipoproteins (HDL's). However, estrogen failed to restore bone back to young adult levels in the established osteoporotic skeleton. Furthermore, long-term estrogen therapy, however, has been implicated in a variety of disorders, including an increase in the risk of uterine cancer, endometrial cancer and possibly breast cancer, causing many women to avoid this treatment. The significant undesirable effects associated with estrogen therapy support the need to develop alternative therapies for osteoporosis that have the desirable effect on serum LDL but do not cause undesirable effects. A second type of pharmaceutical therapy for the treatment of osteoporosis is the use of anabolic agents to promote bone formation and increase bone mass. Although there are a variety of osteoporosis therapies there is a continuing need and a continuing search in this field of art for alternative osteoporosis therapies. In addition, there is a need for bone fracture healing therapies. Also, there is a need for therapy, which can promote bone re-growth into skeletal areas where defects exist such as defects caused or produced by, for example, tumors in bone. Further, there is a need for a safer therapy with fewer side effects. In the art several studies have focussed on mechanisms of osteoclast activation. For example Niida et al (1999) have shown that vascular endothelial growth factor (VEGF) has a positive activity on osteoclast recruitment. One interesting homologue of VEGF is Placental growth factor (PlGF) but its role in bone has been poorly studied (Persico M. G. et al., 1999, Curr Top Microbiol Immunol 237, 31-40). U.S. Pat. No. 5,919,899 describes PlGF and its use in the treatment of inflammatory disorders, wounds and ulcers. Several inhibitors for PlGF signalling, such as antibodies and tetrameric peptides, are known in the art and are disclosed in WO 01/85796, while also Carmeliet et al Nature medicine May 2001 Volume 7 Number 5 pp 575-583 discloses neutralising anti-PLGF antibodies.

The present invention relates to the finding that antagonists of PlGF can be used for the manufacture of a medicament to suppress disorders of bone resorption such as osteoporosis.

AIMS AND DETAILED DESCRIPTION OF THE INVENTION

An object of the present invention is to provide a medicament for the treatment of osteoporosis in higher mammals exhibiting decreased cortical bone mineral density and preventing osteoporosis due to cortical bone mineral density reduction in such mammals. Another object of the invention is to provide pharmaceutical compositions useful in achieving the foregoing object. In our previous studies, the PlGF gene was inactivated in the mouse genome via homologous recombination in embryonic stem (ES) cells (Carmeliet P., 2000, J. Pathol. 190, 387-405, Carmeliet P., 1999, Curr. Interv. Cardiol. Reports 1, 322-335 and Carmeliet P. and Collen D., 1999, Curr. Top. Microbiol. Immunol. 237, 133-158). PlGF (PlGF$^{-/-}$) deficient mice are viable and fertile, and do not exhibit apparent bone defects. However, in the present invention it is shown that upon careful examination of bone histomorphometry, bone remodelling and biochemical analysis of these PlGF KO mice that PlGF plays an unexpected role in the process of bone resorption. It is shown that PlGF deficiency results in decreased bone resorption, low bone turnover and increased trabecular bone mass.

Thus the present invention also demonstrates a method for preventing or inhibiting boss loss or bone mass in a subject, particularly mammalians, including human by inhibiting, preferably locoregional inhibiting the expression of PLGF or its receptor VEGFR-1. Another embodiment is a method for preventing or inhibiting boss loss or bone mass in a subject, particularly mammalians, including human by inhibiting, by inhibiting the VEGFR-1/PlGF signalling pathway.

Moreover the present invention shows that PlGF antagonists can be used for the manufacture of a medicament for treatment of bone disorders and more specifically for the treatment of conditions where there is an enhanced bone resorption such as for example osteoporosis. Thus in one embodiment the invention provides the use of antagonists of PlGF for the manufacture of a medicament to treat bone resorption disorders. Antagonists of PlGF can suppress the bone resorption in said bone resorption disorders. In a specific embodiment said bone resorption disorder is osteoporosis. With "suppression" it is understood that suppression of bone resorption can occur for at least 20%, 30%, 30%, 50%, 60%, 70%, 80%, 90% or even 100%. More specifically the invention relates to the use of molecules (antagonists) to neutralise the activity of PlGF by interfering with its synthesis, translation, dimerisation, receptor-binding and/or receptor-binding-mediated signal transduction. By molecules it is meant peptides, tetrameric peptides, proteins, organic molecules, mutants of the VEGFR-1, soluble receptors of VEGFR-1 and any fragment or homologue thereof having the same neutralising effect as stated above. Also, the invention is directed to anti-PlIGF antibodies and functional fragments derived thereof, anti-sense RNA and DNA molecules and ribozymes that function to inhibit the translation of PlGF, all capable of interfering/or inhibiting the VEGFR-1 signal transduction. By synthesis it is meant trancription of PlGF. Small molecules can bind on the promoter region of PlGF and inhibit binding of a transcription factor or said molecules can bind said transcription factor and inhibit binding to the PlGF-promoter. By PlGF it is meant also its isoforms, which occur as a result of alternative splicing, and allelic variants thereof. As a result of alternative splicing, three PlGF RNAs encoding monomeric human PlGF-1, PlGF-2 and PlGF-3 isoform precursors containing 149, 179 and 219 amino acid residues, respectively, have been described (Cao Y, et al. J Biol Chem. 1996; 271:3154-3162 and Cao Y, et al. Biochem Biophys Res Commun. 1997; 235:493-498).

In normal mouse tissues, only one mouse PlGF mRNA encoding the equivalent of human PlGF-2 has been identified.

To inhibit the activity of the gene or the gene product of PLGF or its receptor VEGFR-1 custom-made techniques are available directed at three distinct types of targets: DNA, RNA, and protein. For example, the gene or gene product of PLGF or its receptor VEGFR-1 can be altered by homologous recombination, the expression of the genetic code can be inhibited at the RNA level by antisense oligonucleotides, interfering RNA (RNAi) or ribozymes, and the protein function can be altered or inhibited by antibodies or drugs.

With "inhibition of expression" to gene expression is understood the inhibition of gene transcription and/or translation of a gene transcript (mRNA) such as for example the PLGF gene or VEGFR-1 gene. Preferably said inhibition is at least 20%, 30%, 40%, 50%, 60%, 70%, 80%, 90% or even higher. With "inhibiting activity" is referred to the protein that is produced such as PLGF or its receptor, in this invention preferably the VEGFR-1 receptor. The inhibition of activity leads to a diminished interaction (e.g. in the case of PLGF with the VEGFR-1 with its receptor and an inhibition of signal transduction). Preferably said inhibition is at least 20%, 30%, 40%, 50%, 60%, 70%, 80%, 90% or even higher.

As specific protein binding ligands, antibodies can be custom-made for virtually any given protein, due to the clonal selection and maturation function of the immune system. Antibodies raised against specific proteins have made possible many technological advances in the field of molecular biology, including modern immunochemistry (Harlow and Lane, Antibodies: A Laboratory Manual, Cold Spring Harbor Laboratory Press, Cold Spring Harbor, N.Y. (1988)). In a specific embodiment of present invention a murine monoclonal antibody against PlGF, disclosed in WO 01/85796, is used for the manufacture of a medicament to treat bone resorption disorders. The term 'antibody' or 'antibodies' relates to an antibody characterised as being specifically directed against PlGF or its receptor VEGF Receptor 1 (VEGFR-1 or FLT-1) or any functional derivative thereof, with said antibodies being preferably monoclonal antibodies; or an antigen-binding fragment thereof, of the F(ab')$_2$, F(ab) or single chain Fv type, or any type of recombinant antibody derived thereof. Preferably these antibodies, including specific polyclonal antisera prepared against PlGF or VEGFR-1 or any functional derivative thereof, have no cross-reactivity to others proteins.

Monoclonal antibodies can for instance be produced by any hybridoma liable to be formed according to classical methods from splenic cells of an animal, particularly of a mouse or rat immunised against PlGF or VEGFR-1 or any functional derivative thereof, and of cells of a myeloma cell line, and to be selected by the ability of the hybridoma to produce the monoclonal antibodies recognising PlGF or VEGFR-1 or any functional derivative thereof which have been initially used for the immunisation of the animals.

Another embodiment is the use of monoclonal antibody against VEGFR-1. A preferred method to produce Anti-VEGFR-1 is for instance by priming rats, for instance Lewis rats (Harlan Sprague-Dawley Inc., Indianapolis, Ind.) with a subcutaneous injection of a antigen comprising a murine VEGFR-1 fragment for instance extracellular domain of VEGFR-1 fused to the Fc-fragment (VEGFR-1-Fc). Emulsified in suitable adjuvant, for instance complete Freund's adjuvant (Sigma). Rats have to receive booster intraperitoneal injections, preferably 4 such booster injections at 2-3-wk intervals with 100 mg of VEGFR-1-Fc. Recombinant human sVEGFR-1-Fc and mouse sVEGFR-1-Fc can be purchased from R&D Systems (Minneapolis, Minn., USA). Rats showing the highest titter of blocking antibody, for instance in a VEGF/VEGFR-1-Fc blocking assays, should consequently be boosted intravenously with such VEGFR-1 antigen (e.g. Flt-FC), preferably with a dose of about 50 mg. About five days later the splenocytes can be harvested and fused to mouse myeloma cells, preferably the P3-X63-Ag8.653 cells. Generation of hybridomas and subcloning was performed according to the current standard protocols available to the men skilled in the art. Hybridomas secreting anti-VEGFR-1 can for instance be selected for binding to soluble VEGFR-1-Fc and negative binding to Fc protein alone in ELISA. The anti-VEGFR-1 can then be selected for inhibition of VEGFR-1-Fc/ligand binding as described below. The binding kinetics of anti-VEGFR-1 can be measured using a Biacore biosensor (Pharmacia Biosensor). Anti-VEGFR-1 can then be produced by culture of hybridoma cells in a suitable medium for instance serum-free medium and the Anti-VEGFR-1 can be purified from conditioned media for instance by a multistep chromatography process. Assessment for purity is generally done by SDS-PAGE and. Immunoreactivity in ELISA with a soluble VEGFR-1 receptor. A negative control rat IgG can be used for comparison. Protein concentration of antibodies are usually determined using the BCA method. The efficiency of such anti-VEGFR-1 to block binding of VEGFR-1 ligands to their receptor can be measured by a VEGFR-1/PlGF blocking assays in plates coated with PlGF. After sequential incubation with VEGFR-1-alkaline phosphatase (AP), pre-incubated with various concentrations of anti-VEGFR-1, and colorigenic substrate, it is possible to measured binding by microtiter plate reading at 405 nm. VEGFR-1-alkaline phosphatase (AP) is obtainable by fusing the extracellular domain of VEGFR-1 to human secretory alkaline phosphatase. Binding of anti-VEGFR-1 to the VEGFR-1 receptor, can be assessed by a standard binding assay for instance by coating microtiter plates by VEGFR-1-alkaline phosphatase and sequential incubation with various concentrations of anti-VEGFR-1, goat anti-rat IgG-HRP and colorigenic substrate to quantified binding by reading on a microtiter Several anti-PlGF and anti-VEGFR-1 antibodies are in the art are available to the public. They are for the anti-humanPIGF antibodies which are available from Genex BioScience Inc (GEA8020-1200 and GEA8020-2) and Alexis corporation or the VEGF Receptor 1 antibodies such as Mouse monoclonal to human VEGF Receptor (ab9541) [Flt-1/EIC] of Abcam Inc. or Novus Biologicals; Anti-Flt-1(VEGFR1) (cat#06-679) with antigen specificity against peptide (GSKLKDPELSLKGTQHIMQA)(SEQ ID NO:1), residues 26-45 of human Flt-1(VEGFR1 of Upstate Charlottesville, Va. 22903 USA; (GEA8021-2 and GEA8021-2) of Genex Biosciences; (cat#RDI-FLT1abrX and cat#RDI-FLT1abrx-1) of Research Diagnostics Inc, Flanders N.J. 07836 US; Mouse anti-humanFLT-1 monoclonal antibody (cat#MAB1664) and rabbit ANTI-FLT-1 affinity purified polyclonal antibody (cat#AB3128) of Chemicon International Temecula, Calif. 92590, USA and Human Fit-1/VEGFR1 Epitope Specific Rabbit Antibody (Cat. #RB-9049-P0, -P1, or -P, Cat. #RB-9049-R7 and Cat. #RB-9049-PCS) of Lab Vision Corporation, CA 94539 USA.

A preferred embodiment for preparing monoclonal antibodies against human PLGF is for instance as follows:

A recombinant human PLGF fusion protein, consisting of the amino acids encoded by PLGF or a fragment thereof is coupled to Glutathione S-transferase (GST) and expressed in *Escherichia coli* and purified by affinity chromatography on immobilised glutathione (Amersham Biosciences). Recombinant human PLGF is also obtainable from R&D Systems Inc. 614 McKinley Place N.E. Minneapolis, Minn. 55413, USA. (264-PG-010, 264-PG-010/CF, 264-PG-050 or 264-PG-050/CF), from Research Diagnostics Inc, Pleasant Hill Road, Flanders N.J. 07836, USA (Recombinant Human PlGF-1: Cat#RDI-300-015 & Cat#RDI-300-016 and Recombinant Human PLGF-2: Cat#RDI-300-019) or from ALEXIS Corporation, CH4415 Lausen, Switzerland (Placenta Growth Factor-2 (human) (recombinant) cat#RLT-300-020) Recombinant human PLGF is mixed with an equal amount of an adjuvant, and an obtained mixture is than subcutaneously administrated to Balb/c male mice (8 weeks old upon the start of immunisation) in an amount corresponding to an amount of PLGF of 100 μg per 1 mouse (priming immunisation). After about 21 days, immunisation can be performed by subcutaneous administration in the same manner as described above (booster immunisation). After 19 days or 30 days from the booster, the mice can administrated through their tail veins with 200 μl of a preparation obtained by diluting human PLGF with PBS (phosphate-buffered physiological saline) to have a concentration of 250 μg/ml (final immunisation). Spleens have than to be excised from the mice after about 3 days from the final immunisation, and they have to be separate into single cells. Subsequently, the spleen cells should be washed with a proper medium, e.g. DMEM medium. On the other hand, suitable mouse myeloma cells (e.g. Sp2/0-Ag14) have to be collected in the logarithmic growth phase, and to be washed with a proper medium, e.g. DMEM medium. The spleen cells and the mouse myeloma cells have to be sufficiently mixed in a plastic tube in a ratio of numbers of the cells of 10:1, followed by addition of 50% (w/v) polyethylene glycol (PEG e.g. of Boehringer Mannheim, average molecular weight: 4000) to perform cell fusion at 37° C. for 7 minutes. After removal of the supernatant solution (by means of centrifugation), the residue is added with HAT medium (DMEM medium containing 10% fetal bovine serum added with hypoxanthine, aminopterin, and thymidine). The residue has to be suspended so that a concentration of the spleen cells of about 5×106 cells/ml is obtained. This cell suspension can than be dispensed and poured into 96-well plastic plates so that one well contains about 100 μl of the suspension, followed by cultivation at 37° C. in 5% carbon dioxide. HAT medium has to be supplemented; for instance in an amount of 50 μl/well on 2nd and 5th days. After that, half volume of the medium can be exchanged every 3 or 4 days in conformity with proliferation of hybridomas.

Screening and Cloning of Hybridomas: Hybridomas, which produce the monoclonal antibody of the present invention, have to be screened for. This has to be done by using, as an index, the inhibitory activity of the monoclonal antibody on the physiological activity possessed by PLGF. Hybridomas, which produced monoclonal antibodies exhibiting reactivity with PLGF's have then to be selected from the selected clones. The obtained hybridomas have then to be transferred to a suitable medium for instance HT medium which is the same as HAT medium except that aminopterin is removed from HAT medium, and cultured further. Cloning can be performed twice in accordance with the limiting dilution method by which stable hybridomas are obtainable.

Production and Purification of Monoclonal Antibodies: 2.6,10,14-Tetramethylpentadecane (e.g. Pristane of Sigma, 0.5 ml) can be intraperitoneally injected into Balb/c female mice (6 to 8 weeks old from the birth). After 10 to 20 days, cells of clones can be (1×106 to 107 cells) suspended in PBS and intraperitoneally inoculated into the mice. After 7 to 10 days, the mice can be sacrificed and subjected to an abdominal operation, from which produced ascitic fluid can be collected. The ascitic fluid can be centrifuged to remove insoluble matters, and a supernatant was recovered and stored at −20° C. until purification Consequently, IgG can be purified from the ascitic fluid supernatant described above by using Hi-Trap Protein-A antibody purification kit (available from Pharmacia, Roosendaal, Netherlands). Namely, the ascitic fluid (2 ml) can be added with Solution A (1.5 M glycine, 3 M NaCl, pH 8.9, 8 ml), and filtrated with a filter for filtration having a pore size of 45 μm (Millipore). After that, an obtained filtrate can applied to a column (column volume: 1 ml) charged with Protein Sepharose HP (produced by Pharmacia) sufficiently equilibrated with Solution A, and the column has be washed with Solution A in an amount of 10-fold column volume. Subsequently, an IgG fraction can be eluted with Solution B (0.1 M glycine, pH 2.8) in an amount of 10-fold column volume. The eluted IgG fraction can be dialysed against PBS. The monoclonal antibodies can be determined for their IgG subclasses by using the purified antibodies obtained in the foregoing, by means of a commercially available subclass-determining kit (trade name: Mono Ab-ID EIA Kit A, produced by Zymed). This method is based on the ELISA method.

The Inhibitory Activities of Monoclonal Antibodies can be tested for complete inhibition of binding of rPlGF to its VEGFR1 receptor. This can for instance measured in an immunofunctional ELISA in which 96-well plates are coated with 100 μl of 1 μg/ml of rmFlt-1/Fc chimera overnight at room temperature in PBS. After blocking for 1 hour with 1% BSA in PBS, 100 μl of a mixture of 70 μl of hybridoma medium pre-incubated with 70 μl of recombinant mPlGF-2 at 10 ng/ml for 2 hours at room temperature is then applied to the plate. A standard of rmPlGF-2 ranging 25 from 20 ng/ml to 156 pg/ml can be included (diluted in PBS-Tween.BSA-EDTA). Plates can then be incubated 1 hour at 370C and 1 hour at room temperature, washed 5 times with PBS-Tween and 100 pi of biotinylated goat anti-murine PlGF-2 at 200 ng/ml can be applied for 2 hours at room temperature. After washing 5 times with PBS-Tween, 1 00 μl of avidin-HRP conjugate (Vectastorin ABC kit) can be applied for 1 hour at room temperature. After washing 5 times with PBS-Tween, the plate can be developed with 90 μl of o-phenylene diamine in citrate phosphate buffer pH 5.0 for 30 minutes and measured at 490 nm.

The present invention also provides inhibiting antibody ligands, which are able to bind to PLGF or its receptor. More preferably, such a ligand should be able to recognise a specific epitope located on PLGF. For instance, the present invention relates to ligands of the above mentioned type, being derived from a monoclonal antibody produced by on purpose immunisation in animals. The present invention also provides an antigen-binding Fab fragment, or a homologue derivative of such fragment, which may be obtained by proteolytic digestion of the said monoclonal antibody by papain, using methods well known in the art. In order to reduce the immunogenicity of the murine anti-PLGF monoclonal antibody, the present invention also includes the construction of a chimeric antibody, preferentially as a single-chain variable domain, which combines the variable region of the mouse antibody with a human antibody constant region—a so-called humanised monoclonal antibody.

The monoclonal antibodies produced in animals may be humanised, for instance by associating the binding complementarly determining region ("CDR") from the non-human monoclonal antibody with human framework regions—in particular the constant C region of human gene—such as disclosed by Jones et al. in Nature (1986) 321:522 or Riechmann in Nature (1988) 332:323, or otherwise hybridised.

The monolonal antibodies may be humanised versions of the mouse monoclonal antibodies made by means of recombinant DNA technology, departing from the mouse and/or human genomic DNA sequences coding for H and L chains or from cDNA clones coding for H and L chains. Alternatively monoclonal antibodies may be human monoclonal antibodies. Such human monoclonal antibodies are prepared, for instance, by means of human peripheral blood lymphocytes (PBL) repopulating of severe combined immune deficiency (SCID) mice as described in PCT/EP 99/03605 or by using transgenic non-human animals capable of producing human antibodies as described in U.S. Pat. No. 5,545,806. Also fragments derived from these monoclonal antibodies such as Fab, F(ab)$'_2$ and ssFv ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses. The antibodies can also be labelled by an appropriate label of the enzymatic, fluorescent, or radioactive type.

A preferred embodiment for preparing of F(ab')2 or monovalent Fab fragments is for instance as follows: In order to prepare F(ab')2 fragments, the monoclonal antibody can be dialysed overnight against a 0.1 mol/L citrate buffer (pH 3.5). The antibody (200 parts) are then digested by incubation with pepsin (1 part) available from Sigma (Saint-Louis, Mo.) for 1 hour at 37° C. Digestion is consequently stopped by adding 1 volume of a 1 M Tris HCl buffer (pH 9) to 10 volumes of antibody. Monovalent Fab fragments can prepared by papain digestion as follows: a 1 volume of a 1M phosphate buffer (pH 7.3) is added to 10 volumes of the monoclonal antibody, then 1 volume papain (Sigma) is added to 25 volumes of the phosphate buffer containing monoclonal antibody, 10 mmol/l L-Cysteine HCl (Sigma) and 15 mmol/L ethylene diaminetetra-acetic acid (hereinafter referred to as EDTA). After incubation for 3 hours at 37° C., digestion is stopped by adding a final concentration of 30 mmol/l freshly prepared iodoacetamide solution (Sigma), keeping the mixture in the dark at room temperature for 30 minutes. Both F(ab')2 and Fab fragments can further be purified from contaminating intact IgG and Fc fragments using protein-A-Sepharose. The purified fragments can finally dialysed against phosphate-buffered saline (herein after referred as PBS). Purity of the fragments can be determined by sodiumdodecylsulphate polyacrylamide gel electrophoresis and the protein concentration can be measured using the bicinchonicic acid Protein Assay Reagent A (Pierce, Rockford, Ill.).

Small molecules, e.g. small organic molecules, and other drug candidates can be obtained, for example, from combinatorial and natural product libraries. To screen for said candidate/test molecules cell lines that express VEGFR-1 may be used and the signal transduction is monitored as described in detail in WO 01/85796 which is herein incorporated by reference. Said monitoring can be measured using standard biochemical techniques. Other responses such as activation or suppression of catalytic activity, phosphorylation (e.g. the tyrosine phosphorylation of the intracellular domain of the receptor) or dephosphorylation of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening. Inhibition of ligand binding to its cellular receptor may, via signal transduction pathways, affect a variety of cellular processes, Cellular processes under the control of the VEGFR-1/PlGF signalling pathway may include, but are not limited to, normal cellular functions, proliferation, differentiation, maintenance of cell shape, and adhesion, in addition to abnormal or potentially deleterious processes such as unregulated cell proliferation, loss of contact inhibition, blocking of differentiation or cell death. The qualitative or quantitative observation and measurement of any of the described cellular processes by techniques known in the art may be advantageously used as a means of scoring for signal transduction in the course of screening.

Random peptide libraries, such as tetrameric peptide libraries further described herein, consisting of all possible combinations of amino acids attached to a solid phase support may be used to identify peptides that are able to bind to the ligand binding site of a given receptor or other functional domains of a receptor such as kinase domains (Lam K S et al., 1991, Nature 354, 82). The screening of peptide libraries may have therapeutic value in the discovery of pharmaceutical agents that act to inhibit the biological activity of receptors through their interactions with the given receptor. Identification of molecules that are able to bind to the VEGFR-1 or PlGF may be accomplished by screening a peptide library with recombinant soluble VEGFR-1 protein or PlGF protein. For example, the kinase and extracellular ligand binding domains of VEGFR-1 may be separately expressed and used to screen peptide libraries. In addition to using soluble VEGFR-1 molecules, in another embodiment, it is possible to detect peptides that bind to cell surface receptors using intact cells. The cells used in this technique may be either alive or fixed cells. The cells will be incubated with the random peptide library and will bind certain peptides in the library to form a "rosette" between the target cells and the relevant solid phase support/peptide. The rosette can thereafter be isolated by differential centrifugation or removed physically under a dissecting microscope.

In another embodiment transdominant-negative mutant forms of VEGF-receptors (e.g. a transdominant-negative receptor of VEGF-R1) can be used to inhibit the signal transduction of PlGF. The use of said transdominant-negative mutant forms of VEGF-receptors is fully described in U.S. Pat. No. 5,851,999. Moreover, the placental soluble fms-like tyrosine kinase 1 (sFlt1), a splice variant of the VEGF receptor Flt1 lacking the transmembrane and cytoplasmic domains, is known to act as a potent PlGF antagonist (Kendall, R. L et al, Biochem Biophys. Res. Commun. 226, 324328 and Shibuya, M. (2001) Cell Struct. Funct. 26, 2535 and soluble VEGFR1 fusion proteins (Aiello, L. P. et al using soluble VEGF-receptor chimeric proteins. Proc Natl Acad Sci USA 92, 10457-10461 (1995)) can be used in vivo to inhibit PLGF activity.

RNA has distinct advantages over small organic molecules when considering its use to inactivate protein function in vivo. An RNA encoding sequence can be linked to a promoter and this artificial gene introduced into cells or organisms. Depending on the regulatory sequence included, this provides a unique way of constructing a time and/or tissue specific suppresser gene. Such RNA expressing genes are usually smaller than protein-coding genes and can be inserted easily into gene therapy vectors. Unlike a foreign or altered protein, RNA is less likely to evoke an immune response. Antisense molecules and ribozymes have been developed as "code blockers" to inactivate gene function, with their promise of rational drug design and exquisite specificity (Altman, "RNase P in Research and Therapy," Bio/Technology 13:327-329 administration will depend on the individual. Generally, the medicament is administered so that the protein, polypeptide, peptide of the present invention is given at a dose between 1 µg/kg and 10 mg/kg, more preferably between 10 µg/kg and 5 mg/kg, most preferably between 0.1 and 2 mg/kg. Preferably, it is given as a bolus dose. Continuous infusion may also be used and includes continuous subcutaneous delivery via an osmotic minipump. If so, the medicament may be infused at a dose between 5 and 20 µg/kg/minute, more preferably between 7 and 15 µg/kg/minute.

In another embodiment antibodies or functional fragments thereof can be used for the manufacture of a medicament for the treatment of the above-mentioned disorders. Non-limiting examples are the commercially available goat polyclonal antibody from R&D Pharmaceuticals, Abingdon, UK or the chicken polyclonal antibody (Gassmann et al., 1990, Faseb J. 4, 2528). Preferentially said antibodies are humanised (Rader et al., 2000, J. Biol. Chem. 275, 13668) and more preferentially human antibodies are used as a medicament.

Another aspect of administration for treatment is the use of gene therapy to deliver the above mentioned anti-sense gene or functional parts of the PlGF gene or a ribozymes directed against the PlGF mRNA or a functional part thereof. Gene therapy means the treatment by the delivery of therapeutic nucleic acids to patient's cells. This is extensively reviewed in Lever and Goodfellow 1995; Br. Med Bull.,51, 1-242; Culver 1995; Ledley, F. D. 1995. Hum. Gene Ther. 6, 1129. To achieve gene therapy there must be a method of delivering genes to the patient's cells and additional methods to ensure the effective production of any therapeutic genes. There are two general approaches to achieve gene delivery; these are non-viral delivery and virus-mediated gene delivery.

In another embodiment PlGF promoter polymorphisms can be used to identify individuals having a predisposition to acquire excessive bone resorption. Indeed, it can be expected that promoter polymorphisms can give rise to much higher or much lower levels of PlGF. Consequently, higher levels of PlGF can lead to a predisposition to acquire an excessive bone resorption disorder such as osteoporosis while much lower levels of PlGF can lead to a protection to acquire excessive bone resorption such as osteoporosis.

Present invention has now demonstrated that a pharmaceutical composition, which comprises an effect amount of a PLGF inhibitor and a VEGFR-1 receptor agonist and a pharmaceutically effective carrier can be used to decrease loss of bone or bone mass and/or for blocking or preventing osteoporosis formation in a subject. Such pharmaceutical composition can be to manufacture a medicament to treat a subject having osteoporosis or at risk of osteoporosis formation.

As used herein, the term "pharmaceutically acceptable carrier" includes any and all solvents, dispersion media, coatings, antibacterial and antifungal agents, isotonic agents, absorption delaying agents, and the like. The use of such media and agents for pharmaceutically active substances is well known in the art. Except insofar as any conventional media or agent is incompatible with the compositions of this invention, its use in the therapeutic formulation is contemplated. Supplementary active ingredients can also be incorporated into the pharmaceutical formulations.

It will be understood by those skilled in the art that any mode of administration, vehicle or carrier conventionally employed and which is inert with respect to the active agent may be utilised for preparing and administering the pharmaceutical compositions of the present invention. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

The therapeutically effective amount of active agent to be included in the pharmaceutical composition of the invention depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg.

The invention provides thus compositions and methods useful for inhibiting, suppressing or ameliorating bone loss or bone mass loss in mammals, including humans. The invention applies to human and veterinary applications. The inventive composition and method have been shown to be especially effective in preventing osteoporosis formation. A new class of pharmaceutical compositions and methods of treatment and prevention of bone loss and bone loss related injury and disease is provided.

A preferred embodiment of present invention is thus the use of antagonists of placental growth factor for the manufacture of a medicament to treat disorders of bone resorption, this treatment of disorders of bone resorption may be a suppression of bone resorption, preferably this bone resorption is osteoporosis. The antagonist inhibiting or suppressing the activity of placental growth factor may be selected from the group consisting of antibodies, peptides, tetrameric peptides, small molecules, anti-sense nucleic acids and ribozymes.

Regarding the method for blocking or preventing osteoporosis in a subject, this invention provides that the subject may be a human. The human may be a patient. The subject may also include other mammals; examples include dogs, cats, horses, rodents, or pigs, rabbits, among others.

The following examples more fully illustrate preferred features of the invention, but are not intended to limit the invention in any way. All of the starting materials and reagents disclosed below are known to those skilled in the art, and are available commercially or can be prepared using well-known techniques.

EXAMPLES

1. Examination of the Bone Phenotype of PIGF Knockout Mice

PIGF deficient mice were described before in Carmeliet P et al. (2001) Nature Medicine. 7:575-583.

1.1. Bone Histomorphometry

Bones were processed for bone histomorphometry as previously described (Daci et al, J Bone Miner Res. 2000, 15:1510-1516). Briefly, the bones were embedded undecalcified in methylmetacrylate and 4 μm thick longitudinal sections were cut with arotary microtome (RM 2155, Leica, Heidelberg, Germany) equipped with a tungsten carbide 50° knife. Sections were stained according to Von Kossa to assess mineralized bone. The measurements were performed in a standardized area comprising most of the proximal tibial metaphysis, using a Kontron Image Analyzing System (Kontron Electronic, KS 400 V 3.00, Eching bei Munchen, Germany). All parameters comply with the recommendations of the Histomorphometry Nomenclature Committee of the American Society for Bone and Mineral Research (Parfitt et al, J. Bone Miner Res 2:595-610, 1987). For immunohistochemistry, bones were fixed in 2% paraformaldehyde in PBS, decalcified in EDTA and embedded in paraffin. Bone sections were immunostained for CD31 as described.

Results:
  An increase of 18% in trabecular bone volume was measured in the proximal tibial metaphysis of newborn PIGF deficient mice compared to WT mice. This increase became more pronounced (+42%; $p<0.05$) in 12 weeks-old PIGF deficient mice.
  Bone histomorphometric studies using double calcein labeling documented a significant decrease in both mineral apposition rate (MAR by 47%) and bone formation rate (BFR by 61%) in 12 weeks-old knock-out mice compared with WT mice
  No vascularisation defects were observed in 12 and 16 week-old PIGF-/- mice, despite the pronounced increase in trabecular bone mass.

1.2. Bone Mineral Density (BMD) and Indices of Bone Remodeling

Trabecular bone mineral density (BMD) was measured in excised tibiae by peripheral quantitative computer tomography (pQCT) (XCT-960M; Nordland Medical Systems Inc.) as described (Dacio et al, cfr supra). Four cross-sections (one cortical at mid-diaphysis and three trabecular at the proximal epiphysis) were scanned, and the data were analysed using a threshold value of 200 $mg/cm^3$ to select for bone and to exclude soft tissue. Cortical and trabecular bones were separated by "concentric peel" with the inner core defined as trabecular bone.

Results: analysis by pQCT showed that the trabecular bone mineral density was increased in PIGF-deficient mice at 12 weeks (+30%; $p<0.05$), whereas cortical bone parameters were only minimally affected. These observations confirmed the histomorphometric data.

1.3. Biochemical Analysis

Serum osteocalcin was measured by the in-house RIA described previously (Bouillon et al. 1992 Clin. Chem 38:2055-2060). Collagen cross-links were quantitated according to an assay previously described (Daci et al. cfr supra). Serum osteocalcin levels measured in PIGF-deficient mice of different ages were on average 30% lower compared to WT mice ($p<0.05$). Urinary excretion of collagen crosslinks was reduced in 12 weeks-old knockout mice by 26% ($p<0.05$).

These data show that deficiency of PIGF in mice results in decreased bone resorption, low bone turnover and increased trabecular bone mass, showing an important role for PIGF in the process of bone resorption.

2. Mouse Models for Osteoporosis

A. Apolipoprotein-E Deficient Mouse

An epidemiological correlation is suggested between osteoporosis and cardiovascular disease independent of age. The basis for this correlation is unknown. Atherosclerosis-susceptible mice receiving a high-fat diet develop osteoporosis as reflected in a decrease in bone mineral content and bone mineral density (Parhami et al. J Bone Miner Res 2001, 16, 182-188). Apolipoprotein-E deficient ($ApoE^{-/-}$) mice were obtained from Dr. J. Breslow (The Rockefeller University, New York, USA). Mice had a mixed genetic background of 75% C57Bl/6 and 25% 129SvJ. Animals were weaned at 4 weeks of age and maintained on normal chow diet for 1 week, after which time they were fed the high fat/high cholesterol diet. For studying the role of PIGF antagonists $ApoE^{-/-}$ mice are intraperitoneally injected three times per week with PIGF antibodies. Both male and female ApoE deficient mice on the high fat/high cholesterol diet showed a decrease in trabecular content by 37% ($p<0.05$) and 12% respectively and a decrease in trabecular density by 42% ($p<0.05$) and 15% respectively. The prevention of the decrease in both parameters is currently being studied in both female and male mice that receive PIGF antibodies (300 μg/ml) which are disclosed in WO01/85796, and with the use of small interference RNAs (RNAi) against the mRNA encoding the PIGF-ligand and/or against the mRNA encoding the Flt-1 receptor.

B. Unloading-induced Bone Loss Mouse Model

Physical inactivity contributes to the development of osteoporosis. The hypothesis is that bone loss induced by inactivity results from decreased bone formation and decreased blood flow, and corresponding hypoxia (Dodd, 1999, Am. J. Physiol. 277: C598-C602). Physical inactivity can be mimicked in mice by a 'hindlimb-unloading' model.

Bone histomorphometry and bone mineral density were measured as described herein above. The Histomorphometry shows that hindlimb unloading reduces trabecular bone volume in WT mice significantly by 50%, while this decrease is only 20% in PlGF null mice (no significant difference could be found in reduction of trabecular bone volume when said PlGF null mice were compared with PlGF null mice with full activity). pQCT analysis shows comparable results for bone mineral density. Thus PlGF deficiency protects mice from bone loss induced by physical activity. This model is currently being applied on wild type mice with and without the application of antibodies against Flt-1 (disclosed in WO01/85796), and with the use of small interference RNAs (RNAi) against the mRNA encoding the PlGF-ligand and/or against the mRNA encoding the Flt-1 receptor.

3. Osteoclast Formation and Function 3.1. Assays for Osteoclast Formation and Function Osteoclast formation was studied using co-cultures of primary osteoblasts and bone marrow cells, treated with 1.25dihydroxyvitamin $D_3$. Briefly, the marrow cavity of the tibiae from 6- to 8-week-old mice was flushed with α-MEM, cells were collected by centrifugation and nucleated cells counted using Türk's solution. In co-culture experiments, primary osteoblasts were plated at $2\times10^4$ cell/well in a 48-well culture plate and 24 h later bone marrow cells were added at $10^5$ nucleated cells/well. Primary osteoblasts derived from the knockout or WT mice were co-cultured with the corresponding bone marrow cells. Co-cultures were treated with $2\times10^{-8}$ M 1.25vitamin $D_3$ or vehicle on day 1, day 3 and stopped at day 6. At the end of the co-culture period, adherent cells were rinsed with PBS, fixed with 4% formaldehyde in PBS for 10 min, treated with ethanol-acetone 50:50 (v/v) for 1 min, air-dried and stained for TRAP. Cells were incubated at room temperature in 0.1 M sodium acetate, pH 5.0 containing naphtol As-MX phosphate and fast red violet LB salt, in the presence of 10 mM sodium tartrate. The number or size of cells staining positively and containing 3 or more nuclei was determined.

Anti-PlGF antibodies were added to the culture at a concentration of 300 μg/ml (antibodies are disclosed in WO01/85796).

In order to determine osteoclast resorbing activity, PlGF-deficient and WT osteoclasts formed in vitro were cultured for 48 h on dentine slices and the resorbed surface was corrected for osteoclast number. To explore the role of PlGF on osteoclast migration, PlGF-deficient and WT osteoclasts were cultured in the upper chamber of culture inserts with collagen-gel coated membranes and their migration to the lower chamber was assessed. Osteoclast survival was studied by counting total osteoclast numbers at different time-points during a 72 h period in cultures of mature osteociasts formed in vitro.

Results:

The total number of osteoclasts formed in bone marrow-osteoblast cocultures of PlGF deficient mice was decreased with 10% (p<0.05) compared to WT co-cultures. When counting only the largest osteoclasts, their number was 50% lower in PlGF deficient co-cultures compared to WT co-cultures. In addition, the percentage of osteoclasts with more than 5 nuclei was decreased significantly. That PlGF participates in osteoclast formation by acting directly on osteoclast progenitors was further demonstrated by studying osteoclast formation in cultures of nonadherent bone marrow cells derived from the knockout and WT mice and treated with M-CSF and RANKL. The number of osteoclasts formed in cell cultures derived from the knockout mice was markedly lower (42±4, n=4 vs. 423±15, n=4, p<0.001) compared with WT cultures.

Size of osteoclasts formed in WT bone marrow-osteoblast co-cultures: (1) without anti-PlGF antibodies: 14260 μm$^2$ and (2) with anti-PlGF antibodies (PI5D11F10 en PI9F7D6—disclose in WO01/85796): 6150 μm$^2$ p<0.001. Osteoclasts derived from knockout or WT mice resorbed dentine similarly, without difference among the two genotypes. No difference was observed among PlGF deficient and WT osteoclasts (12.3±2.4%, n=3 vs. 13.9±1.7%, n=3, respectively) in their ability to migrate and invade the collagen matrix. No difference was observed in the survival of PlGF−/− and WT osteoclasts (71±7%, n=3 vs. 70±2%, n=3, respectively) at 48 h, nor at any other time-point studied (24 h and 72 h). Osteoclast formation and especially the maturation of osteoclast precursors to large multinucleated TRAP positive cells is affected by PlGF as deficiency or low levels of PlGF resulted in decreased size (and number) of osteoclasts. In addition the in vitro data indicate that activity of mature osteoclasts is not affected by PlGF deficiency.

4. Bone Resorption Assay Ex Vivo

To confirm the effect of PlGF on osteoclast formation, bone resorption ex vivo in the presence or absence of PlGF was assessed. Measurement of $^{45}$Ca-release from cultured tibias was performed as previously described (Engsig et al; 2000 J Cell Biol 151, 87, 879-889). Briefly, on day 1, pregnant females (16 days post coitum) were subcutaneously injected with 100 μCi $^{45}$Ca. Twenty-four hours later, tibias were isolated and cultured in media supplemented with ascorbate, glutamate and albumin. It was shown that Ca-release in organ cultures of embryonic long bones was significantly decreased in PlGF deficient explants.

Thus the absence of PlGF clearly reduces osteoclastic bone resorption.

The Ca-release is currently being measured by the addition of PlGF antagonists (PlGF antibodies and RNA interference molecules against PlGF).

5. Osteoblast Formation and Differentiation

Although the data show that PlGF affects osteoclast formation, an effect of PlGF on osteoblast formation and differentiation is not excluded. Therefore we studied osteogenic cell growth, differentiation and mineralization in cultures of mesenchymal stem cells derived from PlGF-deficient and WT mice. Cytochemical staining of mesenchymal cell cultures for total colonies, ALP and matrix mineralization showed that osteogenic cell growth and differentiation proceeded similarly in PlGF-deficient and WT mice, indicating that PlGF deficiency does not affect osteoblast function. The decreases in bone formation parameters observed in vivo most likely reflect the low bone turnover in PlGF deficient mice.

The invention claimed is:

1. A method for treating osteoporosis in an individual, said method comprising administering an antagonist of placental growth factor to that individual in an amount effective to treat said osteoporosis, wherein said antagonist is an anti-Placental Growth Factor antibody or a functionally active fragment thereof.

* * * * *

UNITED STATES PATENT AND TRADEMARK OFFICE
CERTIFICATE OF CORRECTION

| | | |
|---|---|---|
| PATENT NO. | : 7,357,929 B2 | Page 1 of 1 |
| APPLICATION NO. | : 10/519330 | |
| DATED | : April 15, 2008 | |
| INVENTOR(S) | : Peter Carmeliet et al. | |

It is certified that error appears in the above-identified patent and that said Letters Patent is hereby corrected as shown below:

Column 3,
    Line 27, replace "residures," with --residues--.

Column 4,
    Line 56, replace "and." with --and--.

Column 5,
    Line 8, replace "microtiter" with --microtiter plate reader at 450nm.--.
    Line 59, replace "separate" with --separated--.

Column 7,
    Line 38, replace "monolonal" with --monoclonal--.

Column 11,
    Line 38, replace "arotary" with --a rotary--.

Column 13,
    Line 59, replace "osteociasts" with --osteoclasts--.

Column 14,
    Line 16, replace "PI9F7D6-disclose" with --PI9F7D6 disclosed--.

Signed and Sealed this

Seventh Day of April, 2009

JOHN DOLL
*Acting Director of the United States Patent and Trademark Office*